(12) United States Patent
Venkatesan et al.

(10) Patent No.: US 9,247,895 B2
(45) Date of Patent: Feb. 2, 2016

(54) SYSTEMS AND METHODS FOR PERFORMING DEEP BRAIN STIMULATION

(71) Applicant: PACESETTER, INC., Sylmar, CA (US)

(72) Inventors: Lalit Venkatesan, Prosper, TX (US);
Gene A. Bornzin, Simi Valley, CA (US);
Rupinder Bharmi, Canyon Country, CA (US);
Yelena Nabutovsky, Mountain View, CA (US); Riddhi Shah, San Jose, CA (US); Kevin Wilson, McKinney, TX (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/222,301

(22) Filed: Mar. 21, 2014

(65) Prior Publication Data
US 2015/0265180 A1    Sep. 24, 2015

(51) Int. Cl.
A61B 5/06    (2006.01)
A61B 5/055   (2006.01)
A61B 6/03    (2006.01)
A61B 19/00   (2006.01)

(52) U.S. Cl.
CPC ............... *A61B 5/064* (2013.01); *A61B 5/055* (2013.01); *A61B 6/032* (2013.01); *A61B 19/54* (2013.01); *A61B 2019/5466* (2013.01); *A61B 2019/5483* (2013.01)

(58) Field of Classification Search
None
See application file for complete search history.

(56) References Cited

U.S. PATENT DOCUMENTS

| | | | |
|---|---|---|---|
| 6,283,977 B1 * | 9/2001 | Ericsson et al. | 606/130 |
| 7,783,359 B2 * | 8/2010 | Meadows | 607/45 |
| 7,811,294 B2 | 10/2010 | Strommer | |
| 7,925,328 B2 * | 4/2011 | Urquhart et al. | 600/429 |
| 8,343,076 B2 | 1/2013 | Sela | |
| 2009/0118610 A1 * | 5/2009 | Karmarkar et al. | 600/420 |
| 2011/0009879 A1 | 1/2011 | Derrick | |

OTHER PUBLICATIONS

Dostrovsky, Jonathan O. PhD et al., "Mechanisms of Deep Brain Stimulation," Movement Disorders. 2002;17(Supp 3):S63-S68.
Hemm, Simone et al., "Stereotactic implantation of deep brain stimulation electrodes: a review of technical systems, methods and emerging tools," Med Biol Eng Comput. 2010;48(7):611-624.
Volkman, Jens MD et al., "Introduction to the Programming of Deep Brain Stimulators," Movement Disorders. 2002;17(Supp 3):S181-S187.

* cited by examiner

*Primary Examiner* — Brian T Gedeon

(57) ABSTRACT

A method for performing deep brain stimulation (DBS) therapy may include determining a location of a target area of a brain, forming a burr hole through a skull of a patient based on the location the target area, positioning one or more reference members on or within the brain through the burr hole, and acquiring at least one image of the brain having the one or more reference members with at least one imaging sub-system.

18 Claims, 13 Drawing Sheets

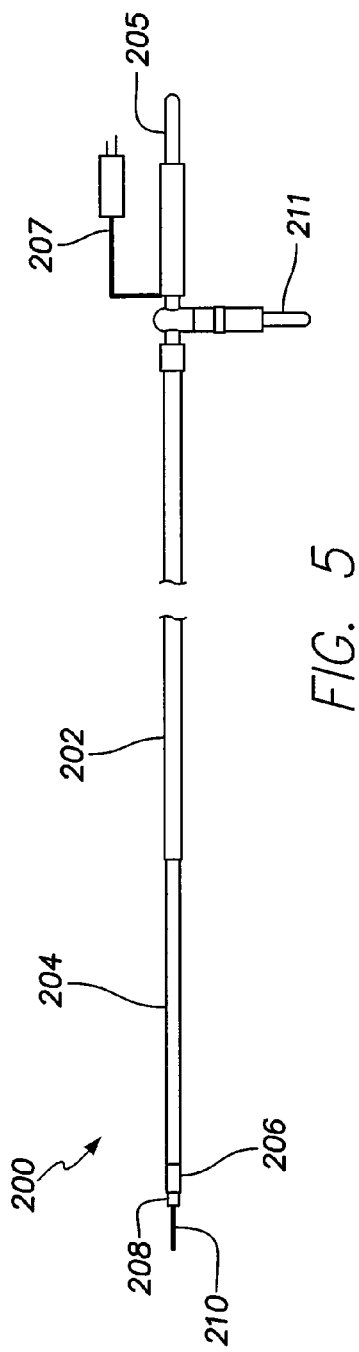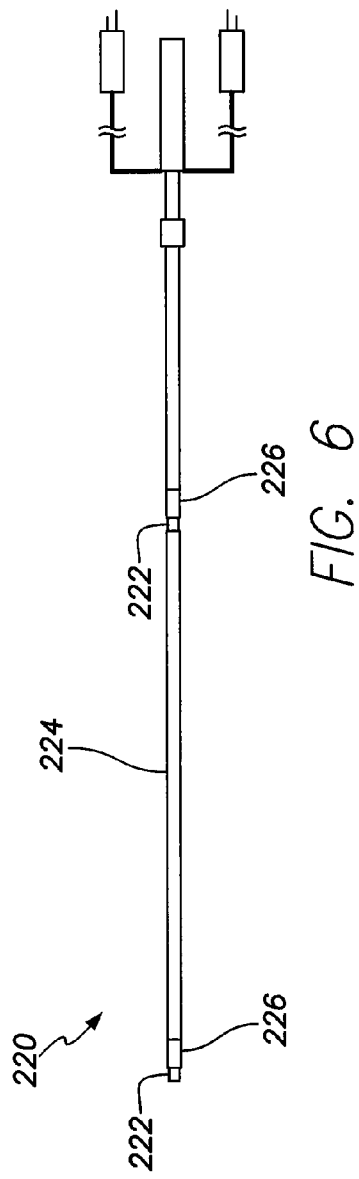
FIG. 5
FIG. 6

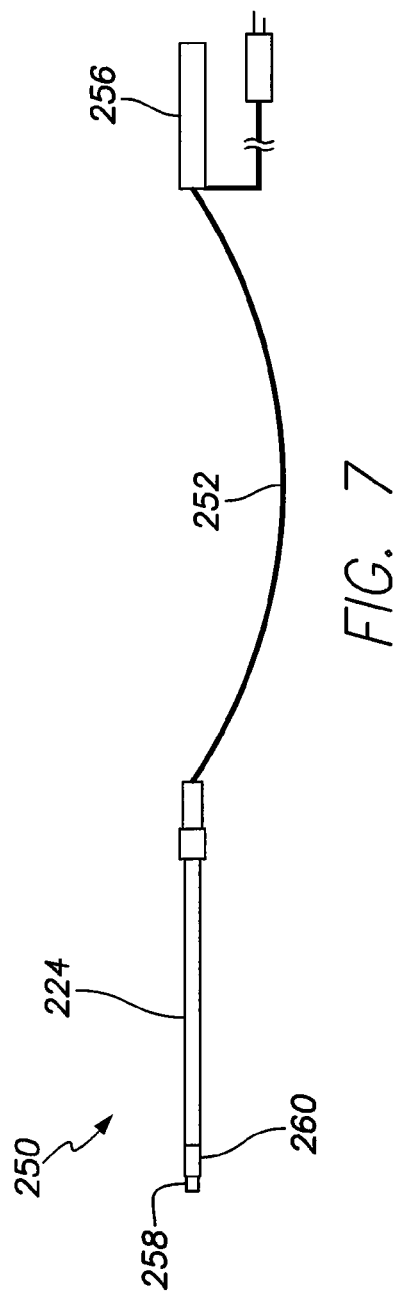
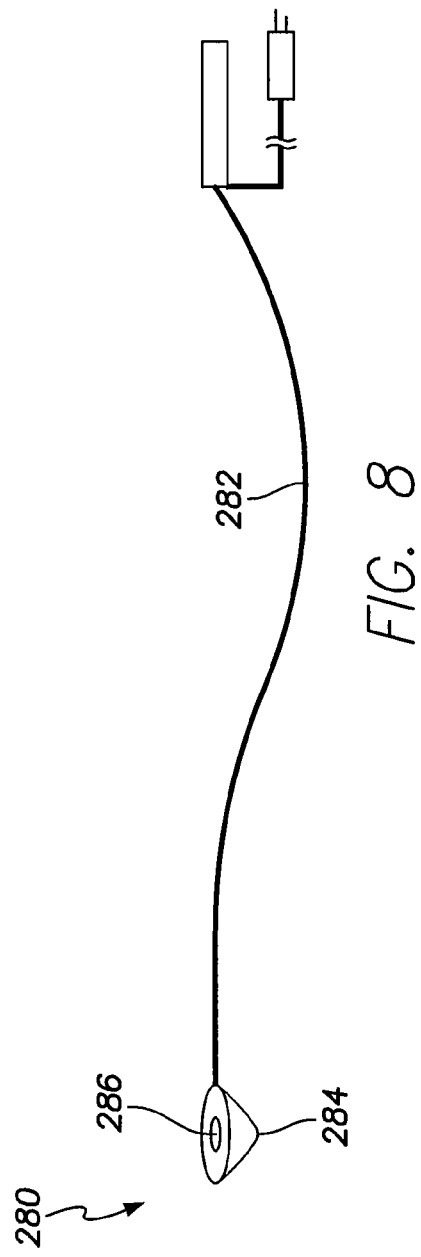

SYSTEMS AND METHODS FOR PERFORMING DEEP BRAIN STIMULATION

FIELD OF THE INVENTION

Embodiments of the present disclosure generally relate to deep brain stimulation systems and methods, and more particularly to systems and methods for positioning probes or leads prior to performing a deep brain stimulation therapy.

BACKGROUND OF THE DISCLOSURE

Deep brain stimulation (DBS) represents a therapy that may be used to treat and relieve various neurological disorders, such as Parkinson's disease, tremors, dystonia, psychiatric illness, and the like. In general, DBS may include electrically stimulating certain areas of the brain to alter or otherwise affect motor function and behavior to alleviate the effects of a neurological disorder. The motor and behavioral effects of brain stimulation typically depend on a location of a stimulating electrode within the brain. Accordingly, DBS generally requires accurate, precise, and safe targeting of brain structure. In order to locate and target specific areas of the brain, surgeons typically rely on a preoperative plan that includes a pathway to the specific target within the brain.

For example, a desired target for treating Parkinson's disease is located in the dorsolateral portion of the sub-thalamic nucleus (STN) of the brain (the entire STN is approximately 3-4 mm in diameter). Other targets such as the globus pallidus or targets in the thalamus are typically no greater than 4-5 mm in diameter. For such small targets, deviation from the target site by as little as 1 mm may not just reduce the effectiveness of treatment, but may also induce undesired side effects such as weakness, altered sensation, slurred speech, double vision, and/or the like. Thus, DBS typically requires accurate surgical planning and targeting of specific locations within the brain.

In general, a DBS process includes positioning a stereotactic frame on a head of a patient, surgical planning, and placing one or more leads or probes within the brain. A DBS process may start with acquiring an image of the brain. For example, a magnetic resonance imaging (MRI) system may acquire an MRI image of the brain. Next, a stereotactic frame is mounted to the skull of the patient. An additional image, such as acquired with a computed tomography (CT) system, is acquired of the patient with the stereotactic frame secured to the skull. A computer then merges the MRI and CT images. A surgeon then uses the merged images to plan the DBS procedure.

During the planning stage, a target area may be identified and located within the merged images. For example, a surgeon may locate the globus pallidus internus or sub thalamic nucleus. The surgeon may then determine implant coordinates of the stereotactic frame that will direct a microelectrode toward the target area.

After the surgical plan including a path to the target area is determined, a burr hole is formed in the skull of the patient. For example, a surgical drill may be used in conjunction with the stereotactic frame to drill a hole through the skull, thereby exposing the brain cortex. The drill may then be removed from the stereotactic frame.

A driving mechanism in conjunction with the stereotactic frame may then be used to move a microelectrode recording probe through a guide tube that passes into the burr hole and into the brain. The microelectrode recording probe is advanced through the guide tube and into the brain while recording neuronal activity during advancement into the brain towards the target area.

Neurons in the target area in the brain typically generate action potentials in known bursting patterns at different frequencies depending upon the respective location. The surgeon may be familiar with such patterns. Thus, the recordings from the microelectrode recording probe may be used to assist the surgeon in determining the correct path to the target area and in determining whether the target area has been reached. For example, neuronal activity recorded by the microelectrode recording probe may be displayed as waveforms on a monitor. Alternatively, or additionally, the acquired neuronal activity may be amplified and output to a speaker. The generated signal, whether shown as waveforms on the display or output through the speaker, allows the surgeon to determine whether or not the microelectrode is on the correct path to the target area. If the surgeon recognizes the generated signal as consistent with a path toward the target area, the surgeon continues to advance the microelectrode on the pre-planned path. If, however, the surgeon determines that the output signal recorded by the microelectrode recording probe is inconsistent with the path toward the target area, the surgeon may discontinue advancement of the microelectrode recording probe, and advance another microelectrode on a different path toward the target area.

Assuming that the microelectrode recording probe is on the correct path, the surgeon may continue to advance the microelectrode recording probe toward the target area until it is a short distance, such as 1-5 mm, from the target area. The surgeon then removes the microelectrode recording probe from the guide tube, and inserts a stimulation lead into the guide tube. The stimulation lead is then advanced into the target area so that electrical pulses from an electrode of the stimulation lead may be directed into the target area.

The surgical plan including the path to the target area may not, however, be accurate. For example, during the drilling of the burr hole, the brain may shift due to pressure changes when air passes into an interior of the skull. Further, the stereotactic frame may also slightly shift, such as if the patient's head moves within the stereotactic frame. Moreover, image superposition and registration algorithm errors may occur. As such, the path to the target area as determined during the surgical planning stage may deviate from a correct path to the target area.

Such errors may cause the target area to be missed, and/or may cause the surgeon to re-advance the microelectrode recording probe in a different and parallel path to the original path determined by the surgical plan. The surgeon may test multiple parallel paths to the target area. For example, the surgeon may test 1-4 additional paths toward the target area with the microelectrode recording probe until a correct path to the target area is found. However, each time a microelectrode recording probe is advanced into the brain, a risk of brain hemorrhage increases.

Accordingly, current systems and methods that are used to plan and test surgical paths to a target area within a brain may not be entirely accurate, and may pose risks of brain hemorrhage, damage, and the like.

SUMMARY

Certain embodiments of the present disclosure provide a method for performing deep brain stimulation (DBS) therapy. The method may include acquiring at least one first image of a brain of a patient with at least one imaging sub-system, determining a location of a target area for therapy in the first image(s), forming a burr hole through a skull of the patient based on the location the target area, positioning one or more reference members on or within the brain through the burr hole, acquiring at least one second image of the brain having the reference member(s), registering a position of the reference member(s) with one or both of the first image(s) and the second image(s) using a registration module, tracking movement of at least one probe within the brain based on the registering operation with a tracking module, and displaying movement of a representation of the probe(s) on the first image(s) and/or the second image(s) based on the tracking operation with a display module. For example, the reference member(s) may be played on a surface of a cortex of a brain prior to imaging. The burr-hole may be drilled after a first image, such as an MRI image, is acquired.

The reference member(s) may include one or more radiopaque fiducials. Optionally, the reference member(s) may include one or more position-detecting coils.

The method may also include positioning a stereotactic frame on a head of the patient. The forming a burr hole operation may include aligning a drill with the head of the patient with the stereotactic frame. The method may also include using a moving mechanism and the stereotactic frame to control movement of the at least one probe into and within the brain.

The probe(s) may include at least one positioning probe having the reference member(s). The positioning probe(s) may also include a recording contact configured to record electrophysiological phenomena. In at least one embodiment, the probe may include at least one therapeutic probe configured to deliver therapeutic energy to the target area.

The method may also include automatically moving the probe(s) into and within the brain toward the target area using a surgical navigation sub-system.

Certain embodiments of the present disclosure provide a system for performing deep brain stimulation (DBS) therapy. The system may include at least one imaging sub-system configured to acquire at least one first image of a brain of a patient. A location of a target area for therapy may be determined from the at least one first image. One or more reference members may be positioned on or within the brain through a pre-formed burr hole. Optionally, the reference member(s) may be positioned on or within the brain prior to imaging and formation of the burr-hole. The imaging sub-system(s) is configured to acquire at least one second image of the brain having the reference member(s). A registration module is configured to register a position of the reference member(s) with one or both of the first image(s) and the second image(s). At least one probe is configured to be moved into and within the brain. A tracking module is configured to track movement of the probe(s) within the brain based on the registration of the position of the reference member(s) with the first image(s) and/or second image(s). A display module is configured to display movement of a representation of the probe(s) on the first image(s) and/or the second image(s) based on the tracked movement of the probe(s).

The at least one imaging sub-system may include a magnetic resonance imaging (MRI) sub-system configured to acquire the first image(s) as at least one MRI image, and a computed tomography (CT) sub-system configured to acquire the second image(s) as at least one CT image. In at least one embodiment, the display module merges the MRI image(s) with the CT image(s) to form a merged image. The display module is configured to display movement of the representation of the probe(s) on the merged image.

Certain embodiments of the present disclosure provide a method for performing deep brain stimulation (DBS) therapy.

The method may include determining a location of a target area of a brain, forming a burr hole through a skull of a patient based on the location the target area, positioning one or more reference members on or within the brain through the burr hole, and acquiring at least one image of the brain having the reference member(s) with at least one imaging sub-system.

BRIEF DESCRIPTION OF THE DRAWINGS

FIG. 5 illustrates a lateral view of a positioning probe, according to an embodiment of the present disclosure.

FIG. 6 illustrates a lateral view of a positioning probe, according to an embodiment of the present disclosure.

FIG. 7 illustrates a lateral view of a positioning probe, according to an embodiment of the present disclosure.

FIG. 8 illustrates a lateral view of a positioning probe, according to an embodiment of the present disclosure.

DETAILED DESCRIPTION

Embodiments of the present disclosure provide systems and methods that may automate phases of deep brain stimulation (DBS) surgery, and/or allow visualization of lead or probe insertion into the brain. Embodiments of the present disclosure provide systems and methods that may automate surgical planning and lead or probe placement, while providing a surgeon a real-time three-dimensional rendered display of a current lead or probe position within the brain, thereby improving positioning of the lead or probe, reducing surgery time, and reducing the likelihood of adverse surgical events, such as brain hemorrhaging.

Figure 1A:
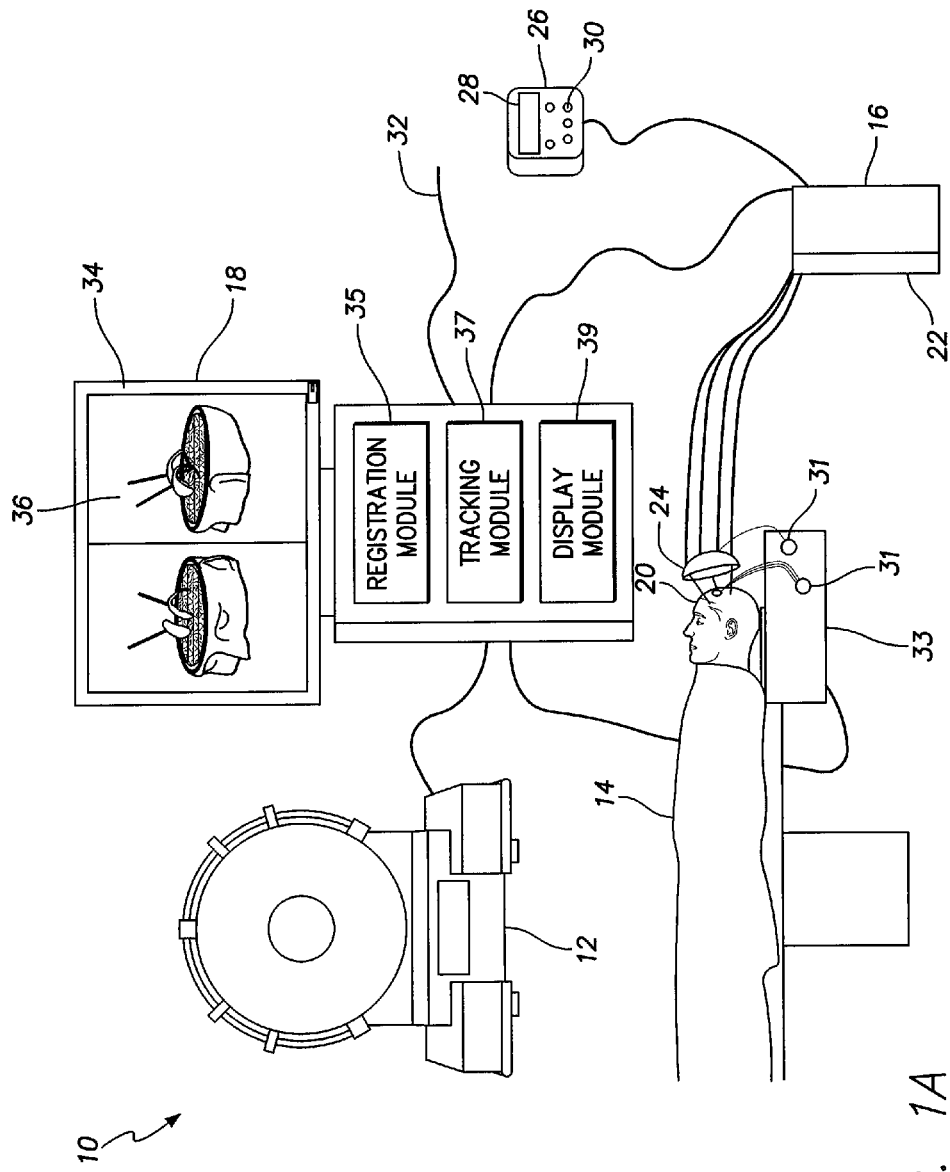
FIG. 1A illustrates a schematic diagram of a deep brain implant system, according to an embodiment of the present disclosure.

FIG. 1A illustrates a schematic diagram of a deep brain implant system 10, according to an embodiment of the present disclosure. The system 10 may include an imaging sub-system 12 configured to acquire images of a patient 14, a deep brain stimulation (DBS) positioning sub-system 16, and a surgical navigation sub-system 18. The imaging sub-system 12 is used to acquire one or more images of the patient 14. The DBS positioning sub-system 16 is used to position probes, such as microelectrode recording probes and therapeutic probes, into a skull 20 of the patient 14. The surgical navigation sub-system 18 may be used in conjunction with the acquired images to allow a surgeon to visualize placement of the probes of the DBS positioning sub-system 16 into the skull 20.

The imaging sub-system 12 may include one or more of an X-ray, fluoroscope, CT, MRI, Positron Emission Tomography (PET), ultrasound, or other such imaging systems. For example, the imaging sub-system 12 may include MRI and CT imaging systems. In general, the imaging sub-system 12 may include a radiation source or generator and a radiation sensor or detector.

The DBS positioning sub-system 16 may include a control unit 22, such as a computer or the like, operatively connected to a stereotactic frame 24 that is configured to be secured to the skull 20 of the patient. The DBS positioning sub-system 16 may also include an interface 26 used to control a driving mechanism that is configured to advance probes into the skull 20 of the patient. For example, the interface 26 may be or include a handheld device having a display 28 and input members, such as keys, a touchscreen, and/or the like. Alternatively, the interface 26 may be or include a keyboard or touchscreen of a computer, tablet, or the like. The DBS positioning sub-system 16 may be or may include a microdrive device including the devices available from Elekta (Stockholm, Sweden).

The surgical navigation sub-system 18 includes a main housing 32, such as a computer workstation, operatively connected to a display 34 that is configured to display images 36 thereon. The display 34 may be or include a monitor, screen, television, or the like, for example. As explained below, the surgical navigation sub-system 18 may be used to electromagnetically track movement of probes of the DBS positioning sub-system 16 before and during a DBS therapeutic procedure. The surgical navigation sub-system 18 may be used to automate surgical planning and lead or probe placement, while displaying a current position of the lead or probe within the brain.

The main housing 32 may contain a registration module 35, a tracking module 37, and a display module 39. The registration module 35 is configured to register reference members, such as fiducials, coils, and/or the like, of a frame, probe, or the like, with one or more reference markers, points, or the like of images of a brain, for example. The tracking module 37 is configured to track movement of a probe, for example, with respect to an area or volume, such as within the brain. The display module 39 is configured to display a representation of the probe, for example, on one or more acquired images on the display, based on the movement of the probe as determined by the tracking module 37.

Each of the modules 35, 37, and 39 may include any processor-based or microprocessor-based system including systems using microcontrollers, reduced instruction set computers (RISC), application specific integrated circuits (ASICs), logic circuits, and any other circuit or processor capable of executing the functions described herein. For example, each of the modules 35, 37, and 39 may be or include at least one processor. The above are exemplary only, and are thus not intended to limit in any way the definition and/or meaning of the term "computer" or "module."

The surgical navigation sub-system 18 may also include a tracking assembly 33 in the vicinity of the patient 14. For example, the tracking assembly 33 may include a housing situated on or underneath a platform on which the patient 14 rests. The tracking assembly 33 may include one or more transmitters 31 configured to radiate a field, such as an electromagnetic field, within the vicinity of the patient 14. The field radiated by the transmitters 31 may be detected by a position detector of a probe, for example, as described below.

Figure 1B:
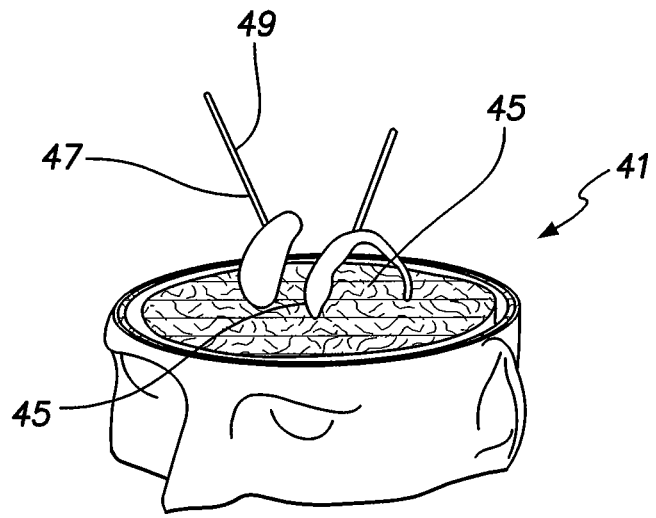
FIG. 1B illustrates an image of an anterior oblique view of a portion of a brain of a patient, according to an embodiment of the present disclosure.
Figure 1C:
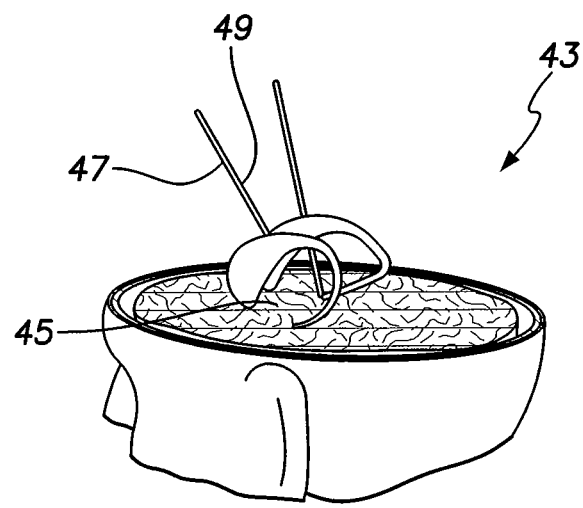
FIG. 1C illustrates an image of a posterior oblique view of a portion of a brain of a patient, according to an embodiment of the present disclosure.

FIG. 1B illustrates an image 41 of an anterior oblique view of a portion of a brain of the patient 14 (shown in FIG. 1), according to an embodiment of the present disclosure. FIG. 1C illustrates an image 43 of a posterior oblique view of a portion of a brain of the patient 14. Referring to FIGS. 1B and 1C, each of the images 41 and 43 may be an image that merges one or more MRI images with one or more CT images. The images 41 and 43 may provide three-dimensional representations of the brain of the patient. The images 41 and 43 may be shown on the display 34 (shown in FIG. 1A).

Each image 41 and 43 may display a target area 45 for therapy and a planned path 47 to the target area 45. A representation 49 of a probe, for example, may be superimposed on the images 41 and 43. As an actual probe moves in space, the surgical navigation sub-system 18 (shown in FIG. 1) tracks the movement of the probe and displays movement of the probe as the representation 49 on the images 41 and 43.

Figure 2A:
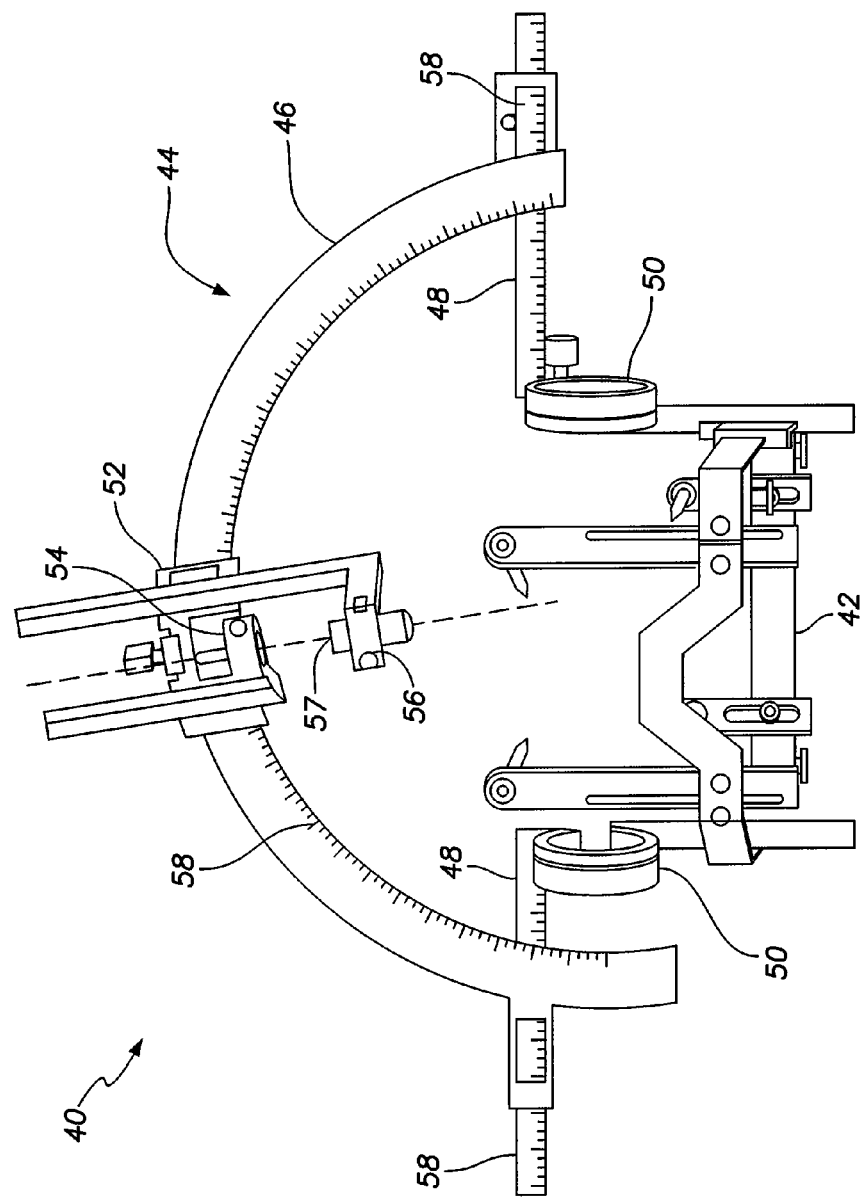
FIG. 2A illustrates a perspective front view of a stereotactic frame, according to an embodiment of the present disclosure.

FIG. 2A illustrates a perspective front view of a stereotactic frame 40, according to an embodiment of the present disclosure. The stereotactic frame 40 is an example of the stereotactic frame 24 shown in FIG. 1A. In order to perform DBS, a surgeon first identifies a target area within a brain of a patient. Identification of the target area may be performed by first securely fixing the stereotactic frame 40 to the skull of the patient and locating the target area through use of acquired images. The position of the target area may be identified in three dimensional coordinates through measurements in relation to radiopaque fiducials that are secured to portions of the stereotactic frame 40.

The stereotactic frame 40 may include an arcuate band 42 configured to be positioned around a portion of the head of the patient. A positioning device 44 is secured to the band 42. The positioning device 44 may include a semi-circular beam 46 that is moveably secured to opposed linear beams 48, which may, in turn, be secured to the band 42 through rotatable mounts 50.

A platform 52 is slidably secured to the semi-circular beam 46. The platform 52 is configured to be moved to different areas of the semi-circular beam 48. The platform 52 may include an upper guide member 54 and a lower guide member 56. The upper and lower guide members 54 and 56 are aligned with respect to an insertion axis 57. The semi-circular beam 46 and the linear beams 48 may include scale markings 58 that are configured to provide an accurate measure of the position of the upper and lower guide members 54 and 56 relative to the platform 52, the angular position of the platform 52 relative to the semi-circular beam 46, and the rotational position of the semi-circular beam 46 relative to the arcuate band 42. As such, the orientation of the insertion axis 57 and any positions relative to the upper and lower guide members 54 and 56 to the arcuate band 46 may be correlated.

The stereotactic frame 40 shown in FIG. 2 is just one example of a frame that may be used with embodiments of the present disclosure. Various other types of frames may be used with respect to embodiments of the present disclosure.

Figure 2B:
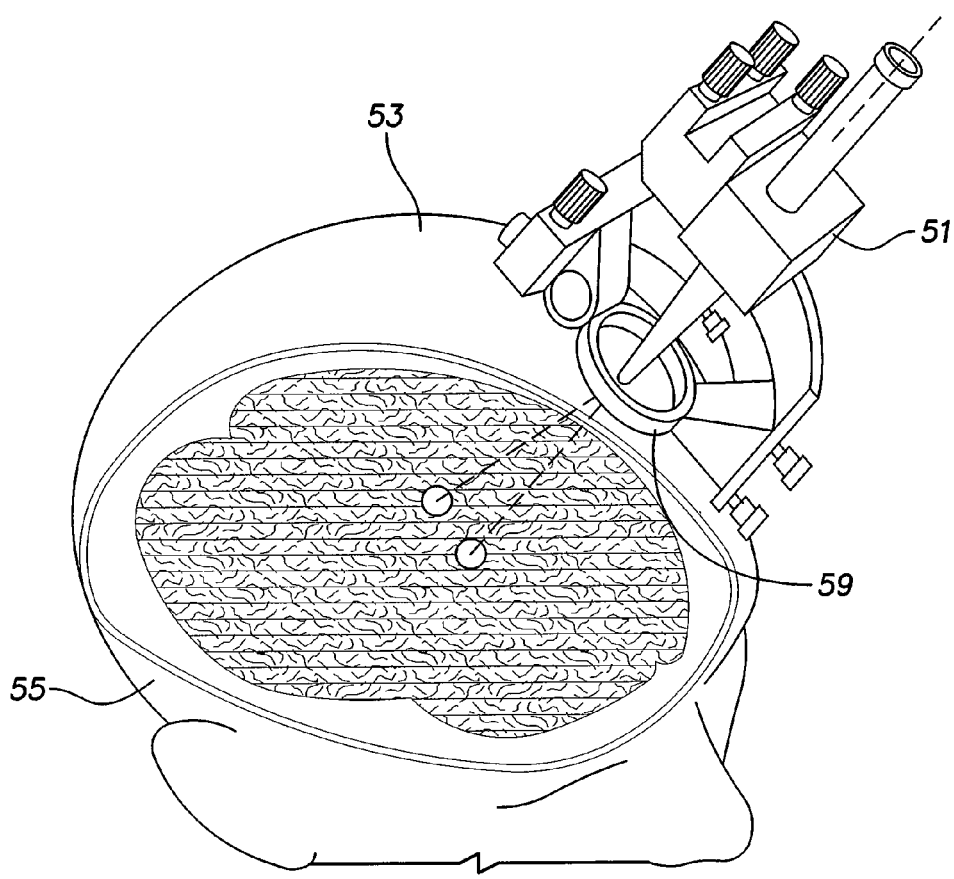
FIG. 2B illustrates a perspective top view of a stereotactic frame secured to a head of a patient, according to an embodiment of the present disclosure.

FIG. 2B illustrates a perspective top view of a stereotactic frame 51 secured to a head 53 of a patient 55, according to an embodiment of the present disclosure. As shown, unlike the frame 40, the frame 51 may include a base 59 that is configured to rest on an outer surface of the head 53, as opposed to wrapping around a portion thereof. The frames shown in FIGS. 2A and 2B represent two examples of frames that may be used with respect to embodiments of the present disclosure. It is to be understood that various other stereotactic frames may be used in place of the frames 40 and 51.

Referring again to FIG. 1A, the stereotactic frame 24 shown in FIG. 1A, an example of which is shown in FIG. 2, is configured to be secured to the skull of the patient. One or more images of the patient with the affixed stereotactic frame 24 are acquired. The stereotactic frame 24 is then used in conjunction with a surgical drill to form a burr hole into the skull, thereby exposing the dura mater (a thick membrane that is the outermost of the three layers of the meninges that surround the brain). After the burr hole is formed, the surgical drill is removed, and the stereotactic frame 24 is then used to precisely position one or more probes into the brain of the patient, which may be accurately guided by the surgical navigation sub-system 18, as explained below. Further, a positioning probe may be positioned through the burr hole to position a reference member, a radiopaque fiducial, or coil on the dura or on or within the brain. A subsequent image may be acquired with the radiopaque fiducial on the dura or on or within the brain in order to register the reference member, radiopaque fiducial, or coil in relation to one or more images of the brain. Notably, because the subsequent image is acquired after the burr hole is formed, any shift of the brain due to the burr hole is accounted for in the acquired image.

Figure 3:
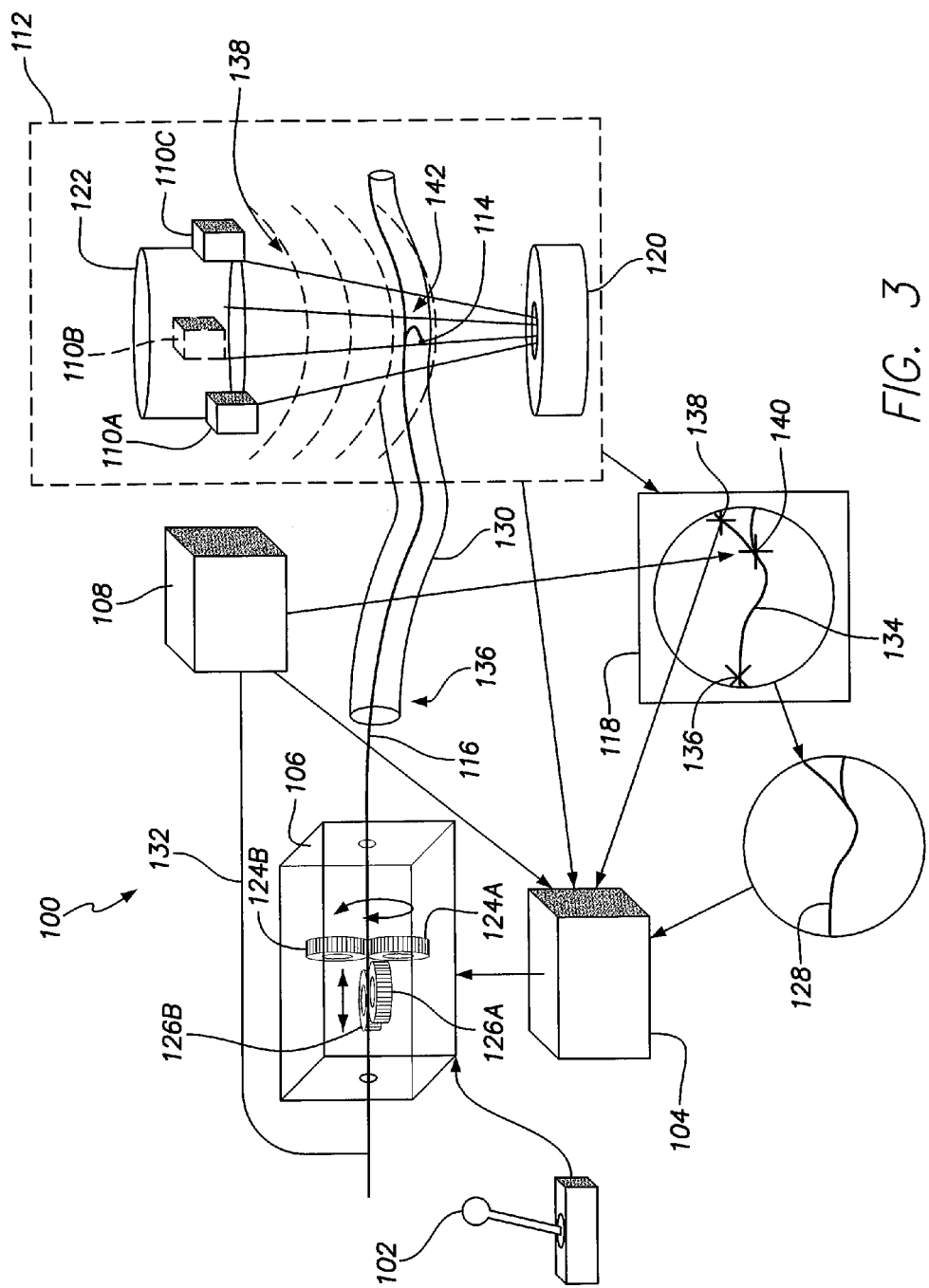
FIG. 3 illustrates a schematic diagram of a surgical navigation sub-system, according to an embodiment of the present disclosure.

FIG. 3 illustrates a schematic diagram of a surgical navigation sub-system 100, according to an embodiment of the present disclosure. The surgical navigation sub-system 100 is an example of the surgical navigation sub-system 18 shown in FIG. 1A. The surgical navigation sub-system 100 may be configured to automatically control the movement of a probe, such as a positioning probe and/or a therapeutic probe, through a guide tube to a target area within a brain of a patient, according to a path within the brain and a current position of the tip of the probe within the guide tube, while employing the current position as a feedback to control the movement. The path which the tip of the probe is to follow may be preplanned and is determined during an imaging session prior to the operational session, by employing a dynamic imager, such as an MRI and/or CT imaging system. The operator, such as a surgeon, can override the automatic operation of the system and revert to the manual mode at any time, while observing a representation of the tip of the probe against an image of the brain.

The probe may be a therapeutic electrode configured to emit energy into patient anatomy, a positioning probe configured to position a radiopaque fiducial on or within the probe, and/or a recording probe, such as a microelectrode recording probe. The probe may include, for example, a guidewire that is configured to be guided to the target area through the guide tube.

The surgical navigation sub-system 100 may include an interface device 102, such as a joystick, a controller 104, a moving mechanism 106, a medical positioning system (MPS) 108, a plurality of transmitters 110A, 110B and 110C, an imaging sub-system 112 (which may be an example of the imaging sub-system 12 shown in FIG. 1A), a position detector 114, a probe 116, and a display 118. The imaging sub-system 112 may include a radiation source or generator 120 and a radiation sensor or detector 122.

The moving mechanism 106 may include a pair of angular movement rollers 124A and 124B, and a pair of linear movement rollers 126A and 126B, and respective moving elements (not shown) such as electric motors, actuators, and the like. However, the moving mechanism 106 may include other, alternative or additional elements (e.g., piezoelectric motors that transfer linear movement through friction). Optionally, the moving mechanism 106 may be disposable. The controller 104 may include a processor (not shown) and a storage unit (not shown) for storing information respective of a path 128, which the probe 116 moves according to, within a guide tube 130.

The moving mechanism 106 may be coupled with the joystick 102 and with the controller 104. The controller 104 may be coupled with the imaging sub-system 112. The MPS 108 may be coupled with the controller 104 and with the transmitters 110A, 110B and 110C. The position detector 114 may be coupled with the MPS 108 by a conductor 132. The display 118 may be coupled with the MPS 108 and with the imaging sub-system 112. The position detector 114 may be located at a distal portion of the probe 116.

During imaging, the body of the patient is located between the radiation generator 120 and the radiation detector 122. The imaging sub-system 112 has at least one degree of freedom, thereby being able to take a plurality of images of the body of the patient from different directions. The imaging sub-system 112 provides a signal to the display 118, respective of an image 134 of the brain.

The path 128 may include an origin 136 and a destination 138, such as a target area, of a distal portion (not shown) of the probe 116 relative to the guide tube 130 within the brain. Both the origin 136 and destination 138 are within a field of view of the imaging sub-system 112. The path 128 may be determined during an imaging session prior to the medical operation, and may be stored in a storage unit. The controller 104 may calculate and construct the path 128, for example, according to a plurality of images obtained of the brain.

Figure 4:
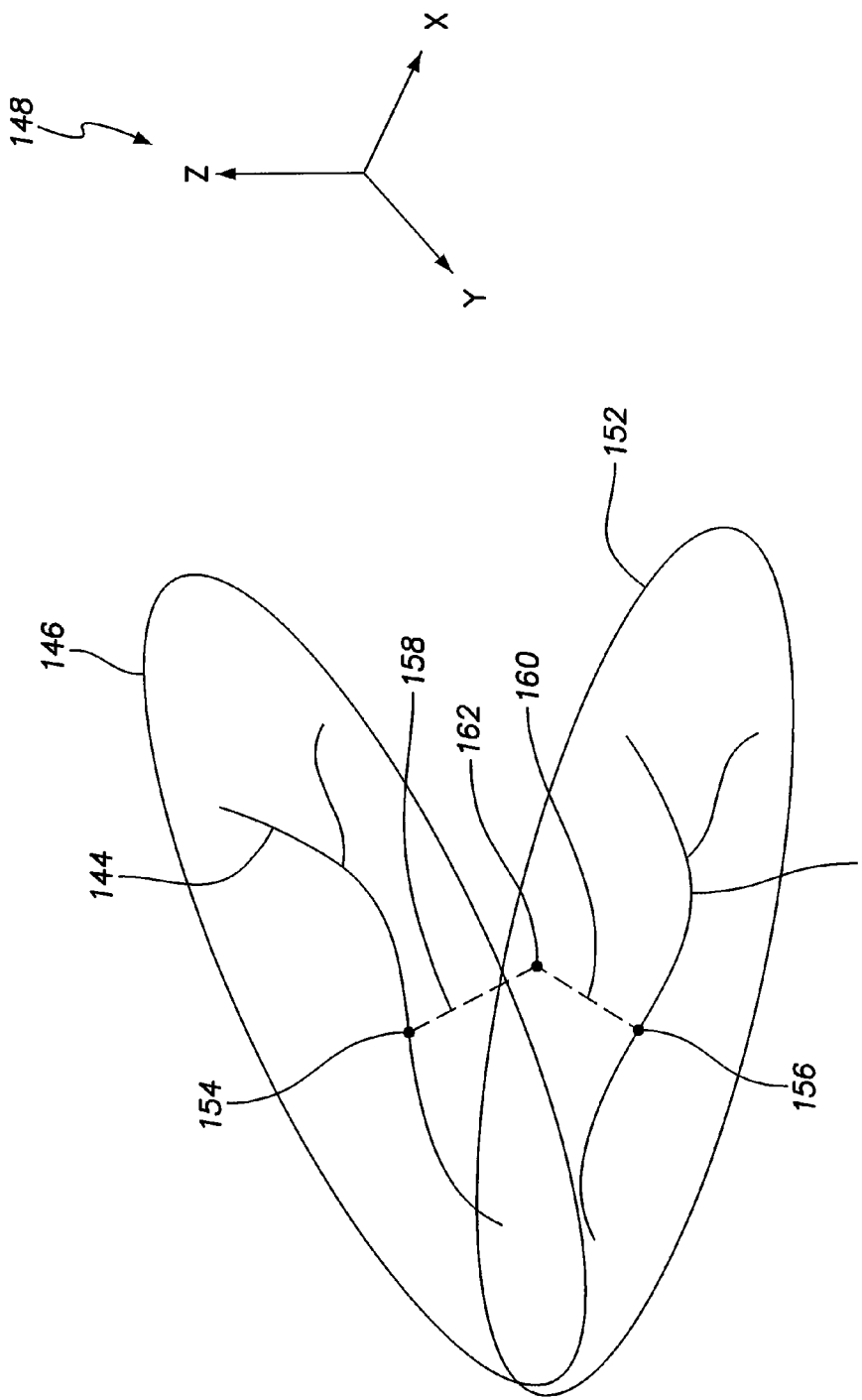
FIG. 4 illustrates first and second images of brain structure, according to an embodiment of the present disclosure.

FIG. 4 illustrates first and second images 144 and 155 of brain structure, according to an embodiment of the present disclosure. Referring to FIGS. 3 and 4, the imaging sub-system 112 may acquire the first image 144 of the brain on an image plane 146 in a three-dimensional coordinate system 148, and the second image 150 of the guide tube 130 on an image plane 152 in the three-dimensional coordinate system 148. The imaging sub-system 112 is aware of the orientation between the image planes 146 and 152 (for example, the angles therebetween). The imaging sub-system 112 identifies a feature 154 of the brain in the first image 144 and a corresponding feature 156 in the second image 150. The imaging sub-system 112 may determine the three-dimensional coordinates of feature 154 (or feature 156) in the three-dimensional coordinate system 148, by determining the intersection of normals 158 and 160 from the features 154 and 156, respectively, to the image planes 146 and 152, respectively, at a point 162. The imaging system 112 performs the above procedure for other features of the brain, thereby constructing the path 128 in three dimensions.

A first transformation model between the three-dimensional coordinate system of the MPS 108 and the three-dimensional coordinate system of the imaging sub-system 112 may be determined. A second transformation model between the three-dimensional coordinate system of the imaging sub-system 112 and a two-dimensional coordinate system of the imaging system 112 may also be determined. The three-dimensional coordinate system of the MPS 108 may be transformed to the three-dimensional coordinate system of the imaging sub-system 112 by applying the first transformation model to the three-dimensional coordinate system of the MPS 108. The three-dimensional transformed coordinate system of the imaging sub-system 112 may then be transformed to the two-dimensional coordinate system of the imaging sub-system 112 by applying the second transformation model to the three-dimensional transformed coordinate system of the imaging sub-system 112.

The surgical navigation sub-system 100 may be used to track and visualize movement of the probe 116 through the brain. The transmitters 110A, 110B, and 110C may be electromagnetic field generators that are configured to generate an electromagnetic field. The position detector 114 may be an electromagnetic field sensor or detector. In response to an electromagnetic field generated by the transmitters 110A, 110B and 110C, the position detector 114 sends a signal to the MPS 108 via a conductor 132, respective of the three-dimensional position of the position detector 114. Alternatively, the position detector 114 may be coupled with the MPS 108 wirelessly and without conductor 132, in which case the position detector 114 sends the position signal to the MPS 108 wirelessly.

The MPS 108 determines the coordinates of the position detector 114 according to the signal received from the position detector 114. The MPS 108 sends a signal respective of the coordinates of the position detector 114 to the controller 104 in the three-dimensional coordinate system of the MPS 108. The MPS 108 sends a signal respective of the coordinates of the position detector 114 to the display 118.

Throughout the medical operation, the display 118 may show an image 134 of an operational region of the brain (e.g., a section between the origin 136 and the destination 138) according to a signal received from the imaging system 112. The display 118 may also display a representation 140 of the current location of position detector 114 (i.e., the distal portion of probe 116), superimposed on the two-dimensional image 134, according to the signal received from MPS 108. Alternatively, the current location of the position detector can be superimposed on a three-dimensional image of the guide tube.

The surgical navigation sub-system 100 may be further described with respect to U.S. Pat. No. 7,811,294, entitled "Automatic Guidewire Maneuvering System and Method," which is hereby incorporated by reference in its entirety. The surgical navigation sub-system 100 may be used to visualize movement of the probe 116 with respect to one or more images of the brain. While the surgical navigation sub-system 100 may be used to automatically move the probe 116 according to a surgical plan, the surgical navigation sub-system 100 may optionally be used to simply superimpose an image of the probe with respect to the image(s) of the brain in order to track movement of the surgical probe with respect to the brain.

Referring again to FIG. 1A, one or more images of the brain may be acquired through the imaging sub-system 112. The imaging sub-system 112 may then be used to image the brain while the patient 14 is wearing the stereotactic frame 24. The stereotactic frame 24 may include one or more radiopaque fiducials that appear in the image of the brain. The positions of the radiopaque fiducials within the images provide reference points. The reference points in the images may be registered (such as by the registration module 35) with features, markers, landmarks, or the like so that movement of a probe having a position detector or sensor (as described with respect to FIG. 3, for example) may be tracked in relation to the images.

As described below, embodiments of the present disclosure may also position one or more radiopaque fiducials within the brain during the imaging process. As such, the radiopaque fiducials of the stereotactic frame and those within the brain appear on the images and are used to register the positions with respect to features on the images.

FIG. 5 illustrates a lateral view of a positioning probe 200, according to an embodiment of the present disclosure. The positioning probe 200 may be used to position one or more radiopaque fiducials on or within a brain, and may also include a microelectrode recording device, for example. The positioning probe 200 includes a guide tube 202 defining an internal passage through which an electrode lead 204 is positioned. The guide tube 202 may be formed of a rigid material, such as stainless steel. Optionally, the guide tube 202 may be formed of various other materials, such as flexible plastic.

The electrode lead 204 may be covered with polymide tubing, for example. The electrode lead 204 may be operatively connected to and in communication with the DBS positioning sub-system 16 through a DBS connector 205. A position detector 206 is secured to a distal end of the electrode lead 204. The position detector 206 may include one or more coils that are configured to detect a radiated field, such as an electromagnetic field. The position detector 206 may be operatively connected to and in communication with the surgical navigation sub-system 18 (shown in FIG. 1A) through a navigation connector 207.

A radiopaque fiducial 208, such as a ball formed of platinum, titanium, or the like, may also be secured to the electrode lead 204. For example, the radiopaque fiducial 208 may be secured to a distal end of the position detector 206. Alternatively, the radiopaque fiducial 208 may be located at various other portions of the positioning probe 200. Further, the positioning probe 200 may include more radiopaque fiducials 208 than shown in FIG. 5. As an example, an additional radiopaque fiducial may be positioned at a mid-point of the electrode lead 204. When imaged by the imaging sub-system 12 (shown in FIG. 1A), the radiopaque fiducials prominently appear in the acquired images.

The positioning probe 200 may also include a recording contact 210, such as micro-recording electrode formed of Tungsten. The recording contact 210 may be located at a distal tip of the electrode lead 204. The recording contact 210 is configured to record electrophysiological phenomena such as frequencies, for example, emitted by structures within the brain. The recording contact 210 may be operatively connected to and in communication with the DBS sub-system 16 (shown in FIG. 1A) through a recording connector 211. Alternatively, the positioning probe 200 may not include the recording contact 210.

FIG. 6 illustrates a lateral view of a positioning probe 220, according to an embodiment of the present disclosure. The positioning probe 220 is shown without a guide tube, although it is to be understood that the positioning probe 220 may include or be moveably retained within a guide tube.

The positioning probe 220 is similar to the positioning probe 200 shown in FIG. 5, except that the positioning probe 220 may include a radiopaque fiducial 222 at a distal tip of an electrode lead 224, as well as a radiopaque fiducial 222 at an intermediate portion of the electrode lead 224. The positioning tube 220 may also include multiple position detectors 226 along its length. The positioning probe 220 may not include a recording contact.

FIG. 7 illustrates a lateral view of a positioning probe 250, according to an embodiment of the present disclosure. The positioning probe 250 is similar to the positioning probe 220 shown in FIG. 6, except that the positioning probe 250 may include a flexible wire 252 that connects a rigid electrode lead 254 to connecting interfaces 256. A radiopaque fiducial 258 and a position detector 260 may be located at a distal tip of the rigid electrode lead 254.

FIG. 8 illustrates a lateral view of a positioning probe 280, according to an embodiment of the present disclosure. The positioning tube 280 may include a flexible electrode lead 282 having a position detector 284 that retains a radiopaque fiducial 286.

Figure 9:
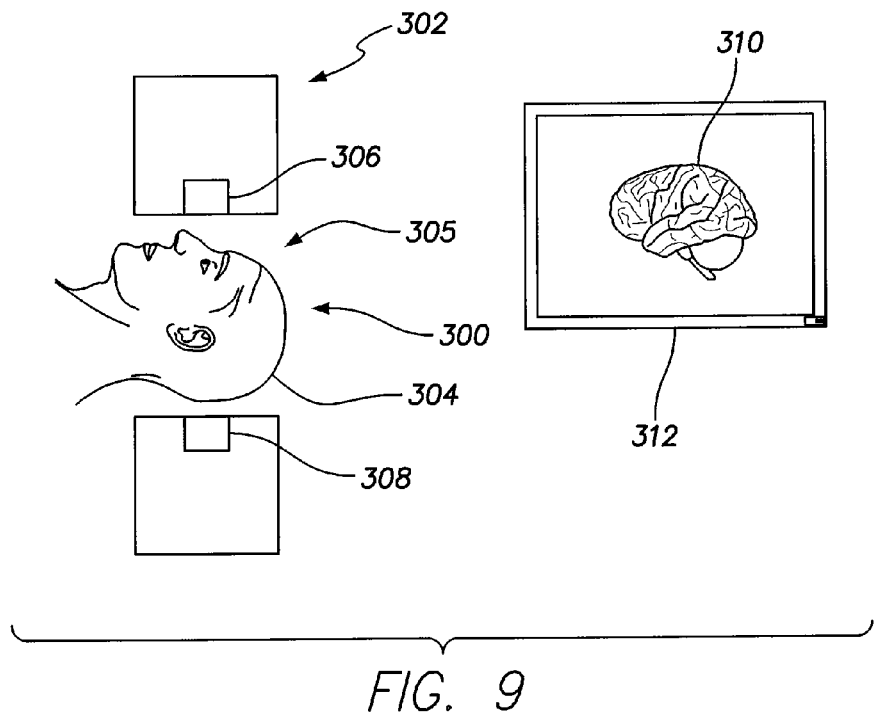
FIG. 9 illustrates a simplified diagram of a patient being imaged by a first imaging sub-system, according to an embodiment of the present disclosure.

FIG. 9 illustrates a simplified diagram of a patient 300 being imaged by a first imaging sub-system 302, according to an embodiment of the present disclosure. The head 304 of the patient 300 is positioned within an imaging area 305 located between an emitter 306 and a detector 308. The first imaging sub-system 302 may be an MRI sub-system that is configured to acquire an image 310 of the brain of the patient 300 and output to a display 312. The image 310 is used to determine a location of the target area within the brain that is to be treated with therapeutic energy. After the image 310 is acquired, a stereotactic frame is positioned on the patient 300.

Prior to imaging, anatomical markers may be positioned on the patient's head to assist in accurately registering the image with a subsequent image of the patient. The markers may be placed on the dura mater, a cortical surface, or deep within the brain. A radiopaque marker of a positioning probe, for example, may also be placed within the brain and correlated with the anatomical markers.

Figure 10:
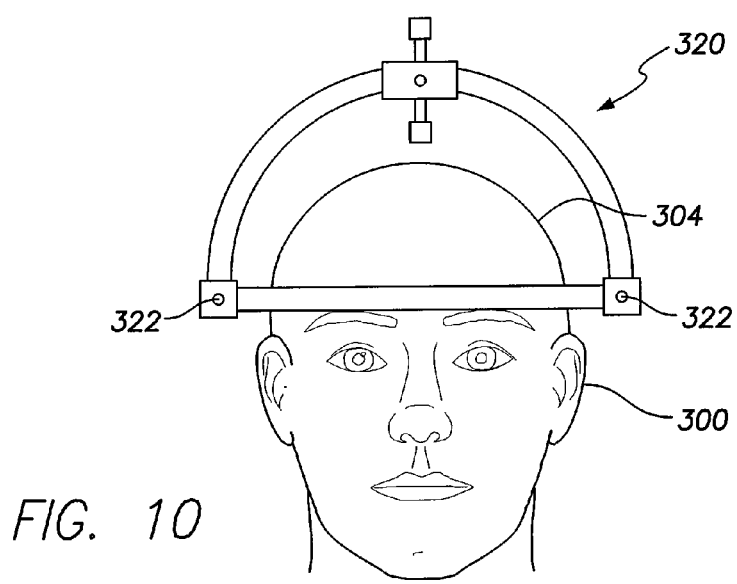
FIG. 10 illustrates a simplified diagram of a stereotactic frame secured to a patient, according to an embodiment of the present disclosure.

FIG. 10 illustrates a simplified diagram of a stereotactic frame 320 secured to the patient 300, according to an embodiment of the present disclosure. Any type of stereotactic frame configured for DBS may be used. The stereotactic frame 320 may include one or more radiopaque fiducials 322.

Figure 11:
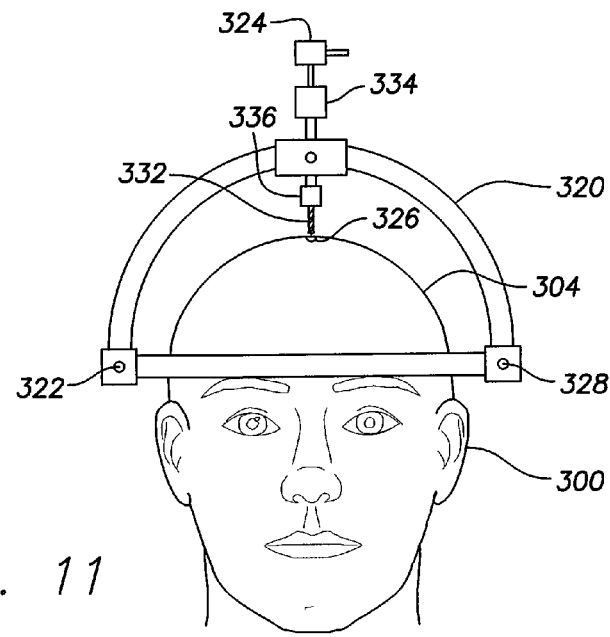
FIG. 11 illustrates a simplified diagram of a surgical drill being used in conjunction with a stereotactic frame to drill a burr hole through a skull of a patient, according to an embodiment of the present disclosure.

FIG. 11 illustrates a simplified diagram of a surgical drill 324 being used in conjunction with the stereotactic frame 320 to drill a burr hole 326 through a skull 328 of the patient 300, according to an embodiment of the present disclosure. The location of the burr hole 326 is determined through the acquired image 310 (shown in FIG. 9). The surgical drill 324 includes a main housing 330 operatively connected to a drill bit 332 that is guided into position through one or more guide members 334 and 336 of the stereotactic frame 320. Once in position, the surgical drill 324 is operated to form the burr hole 326.

Once the burr hole 326 is formed, the surgical drill 324 is removed from the patient 300 and the stereotactic frame 320. The burr hole 326 may be formed through the skull 328 to expose the dura mater. Notably, as the burr hole 326 is formed, the brain may shift. The burr hole 326 is used in order to allow a positioning probe, such as any of the positioning probes described above, to be positioned therethrough. Alternatively, instead of using a positioning probe, a position detector, such as a coil used to detect the presence of an electromagnetic field, and/or a radiopaque marker may be positioned on the dura mater, on the cortex of the brain, or within the brain.

Figure 12:
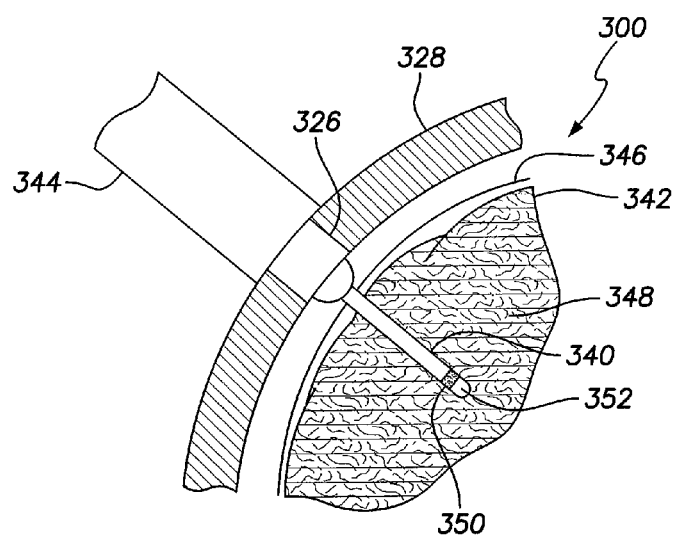
FIG. 12 illustrates a simplified diagram of a positioning probe being inserted into a brain of a patient, according to an embodiment of the present disclosure.

FIG. 12 illustrates a simplified diagram of a positioning probe 340 being inserted into the brain 342 of the patient 300, according to an embodiment of the present disclosure. The positioning probe 340 may be guided into and through the burr hole 326 through the stereotactic frame 320 (shown in FIG. 11, for example). A driving mechanism 344 advances the positioning probe 340 into the brain 342. As shown in FIG. 12, the burr hole 326 is formed through the skull, thereby perforating the dura 346 and exposing the cortex 348.

The positioning probe 340 may include a position detector 350 and one or more radiopaque fiducials 352. The radiopaque fiducial 352 may be inserted into the brain 342 proximate to the basal ganglion, for example, or positioned on an outer surface of the brain 342 underneath the dura 346. The radiopaque fiducial 352 may be used to register a position within the brain to a subsequent image, and/or a relative location of the position detector 350 to a subsequent image, such as a CT scan. Because the radiopaque fiducial 352 is positioned or within the brain 342 after formation of the burr hole (and any brain shift), the radiopaque fiducial 352 accounts for any brain shift and allows for registration of a coordinate system of the surgical navigation sub-system with the acquired image(s).

As shown, the radiopaque fiducial 352 may be located on the positioning probe 340. Alternatively, a separate and distinct radiopaque fiducial 352 may be implanted, either temporarily or permanently, on or within the brain 340.

The radiopaque fiducial 352 and the position detector 350 may be positioned on the dura mater or on or within the brain 342 after the burr hole 326 is formed. The radiopaque fiducial 352 may include three asymmetric fiducial members in order to increase precision of the registration. When three fiducial members are established in space, a resulting registration is three-dimensional. The multiple fiducial members may be used to orient the radiopaque fiducial within a subsequent image and the registration module 35 of the surgical navigation sub-system 18 may perform a registration based on the multiple fiducial members that provide direction and orientation of the radiopaque fiducial 352. Further, the position detector 350 may include multiple coil members that appear in a subsequent image to also increase precision of the registration. Any brain shift occurs as the burr hole 326 is formed, but before the radiopaque fiducial 352 is positioned. As such, deviations within the images and/or registration of the images with the radiopaque fiducial markers are eliminated, minimized, or otherwise reduced. The radiopaque fiducial 352 positioned within the brain allows the registration module 35 of the surgical navigation sub-system 18 to register the brain geometry to a point on a subsequent acquired image of the brain after any brain shift.

Referring to FIGS. 5-8, multiple positioning probes may be used in conjunction with one another to provide multiple radiopaque fiducials, markers, features, or the like that may be established within space. The multiple radiopaque fiducials may then be used to provide three-dimensional registration with one or more acquired images.

Figure 13:
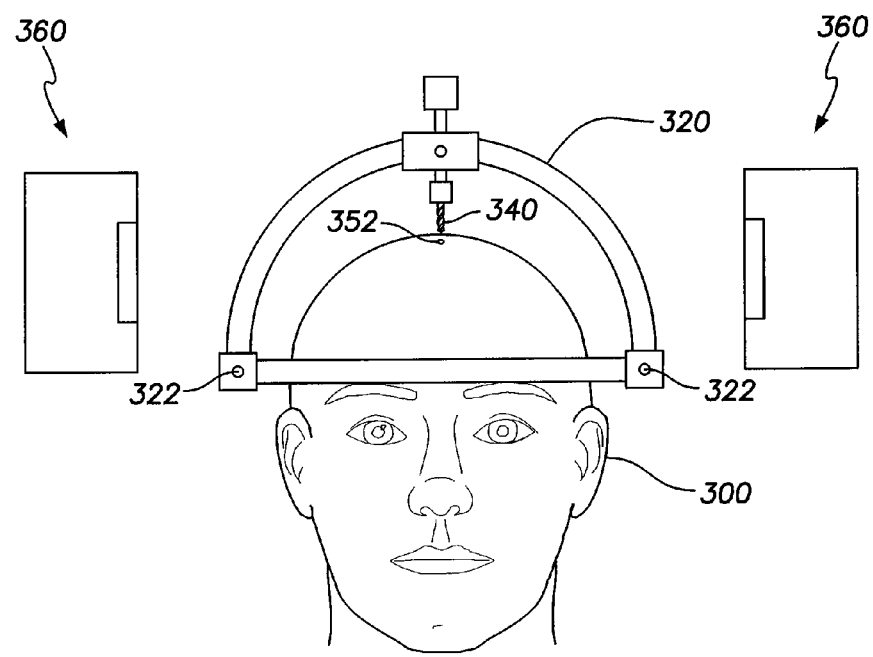
FIG. 13 illustrates a simplified diagram of a patient with a secured stereotactic frame being imaged by an imaging sub-system, according to an embodiment of the present disclosure.

FIG. 13 illustrates a simplified diagram of the patient 300 with the secured stereotactic frame 320 being imaged by an imaging sub-system 360, according to an embodiment of the present disclosure. The imaging sub-system 360 may be a CT scanner, for example. Alternatively, the imaging sub-system may be the same as the imaging sub-system shown in FIG. 9. Notably, the imaging process shown in FIG. 13 occurs after the burr hole 326 is formed. As such, the imaging process occurs subsequent to any brain shift.

As shown, the patient 300 is imaged with the positioning probe 340 secured in place by the stereotactic frame 320. As such, the radiopaque fiducial 352 is secured in position with the brain of the patient 300. As the imaging sub-system 360 acquires an image(s) of the patient 300, the radiopaque fiducials 322 of the stereotactic frame 320 and the radiopaque fiducial 352 secured within the brain of the patient 300 appear on the resulting image(s). While only one radiopaque fiducial 352 is shown secured within the brain of the patient, additional radiopaque fiducials may be secured within the brain.

Prior to imaging, anatomical markers may be positioned on the patient's head to assist in accurately registering the image with the radiopaque fiducials and the previously-acquired image. The registration module 35 (shown in FIG. 1) registers the images with one another through registration of the anatomical markers and the radiopaque fiducials, features, markers, and/or the like shown in the images.

Referring to FIGS. 1A and 9-13, after the image(s) of the patient 300 are taken, the surgical navigation sub-system 18 may merge the initial images of the patient 300 (acquired with respect to FIG. 9) with the subsequent images (acquired with respect to FIG. 13). The target area may then be identified in the merged images. The coordinates of the target area may be determined, at least in part, through reference of the fiducials 322 of the stereotactic frame 320 and the radiopaque fiducial 352 within the brain of the patient 300.

The registration module 35 of the surgical navigation sub-system 18 registers the image acquired after the burr hole 326 is formed with the fiducial(s) 352 within the brain (and with the fiducials 322 of the stereotactic frame 320). The stereotactic frame 320 may also include coil references that are used to register an exact location of the stereotactic frame 320 relative to the fiducial 352 within the brain of the patient 300.

Once the images are merged and the surgical navigation sub-system 18 registers the images with the fiducials 322 and 352, the tracking module 37 of the surgical navigation sub-system 18 may track movement of the positioning probe 340 within the brain and the display module 39 may superimpose the movement of the positioning probe 340 on the image(s) of the brain shown in the display 34. The positioning probe 340 may be automatically advanced based on a pre-planned path using a driving mechanism secured to the stereotactic frame 320. The positioning probe 340 is tracked by the surgical navigation sub-system 18 as it advances into the brain. A surgeon may use the interface 26 to control a rate and progress of the positioning probe 340 through the brain.

The driving mechanism 344 (shown in FIG. 12) may be used to advance the positioning probe 340 further into the brain toward the target area. Once or more transmitters (such as electromagnetic field transmitters) are positioned around the patient 300. The position detector 350 secured to the positioning probe 340 detects the presence of the transmitted radiation, such as an electromagnetic field, which is then received by the surgical navigation sub-system 18 to detect the exact position of the position detector 350, and therefore the positioning probe 340 within the brain of the patient. At the same time, a recording contact (such as the recording contact 210 shown in FIG. 5) may be used to record electrophysiological phenomena consistent with the target area of the brain. The surgical navigation sub-system 18 is used to track and display the position of the positioning probe 340 in relation to the acquired images of the brain in real time, relative to the target area. If the trajectory is determined to be off-target based on either the surgical navigation sub-system 18 or the recording contact, the positioning probe 340 may be removed and re-positioned according to a corrected path to the target area. Alternatively, the recording contact may not be used. Instead, the tracking and positioning of the positioning tube 340 may be based solely on operation of the surgical navigation sub-system 18.

Use of the recording contact in conjunction with the surgical navigation sub-system during advancement of the positioning probe through the brain allows for simultaneous micro-electrode recording (through the recording contact) and real-time positioning (through the surgical navigation sub-system). As such, embodiments of the present disclosure may provide real-time visualization of the positioning probe on the merged image scans (such as merged MRI and CT scans) as the positioning probe approaches the target area. Three-dimensional visualization of a representation of the positioning probe on the merged images in conjunction with the micro-electrode recordings may be concurrently output to a surgeon. Real-time visualization (through the surgical navigation sub-system) helps the surgeon to identify the cortical geometry as the positioning probe approaches the target area and may therefore be used to avoid hitting undesired locations, such as an optical nerve track or a blood vessel.

The surgical navigation sub-system tracks the location of the stereotactic frame in relation to the patient, as well. As such, any frame shift may be corrected based on an analysis of the fiducials of the frame in relation to the fiducial within the brain to ensure proper trajectory toward the target area of the brain.

Further, the actual position of the recording contact in relation to the radiopaque fiducial on the positioning probe is constant and stable. As such, when the positioning probe is placed in the brain, if the trajectory registration deviates from the target area of the brain due to cumulative unpredictable error, a projected track of the positioning probe may be displayed. As such, a surgeon may be able to correct the trajectory in real time.

After the positioning tube 340 has been accurately positioned based on consultation with the output of the surgical navigation sub-system and confirmed by agreement with the output of the recording contact, a surgeon may remove the positioning probe 340 from a guide tube, and insert a therapeutic probe into the guide tube to contact the target area. The surgeon may then evaluate the position of therapeutic probe by checking the patient's response to stimulation of the target area.

Figure 14:
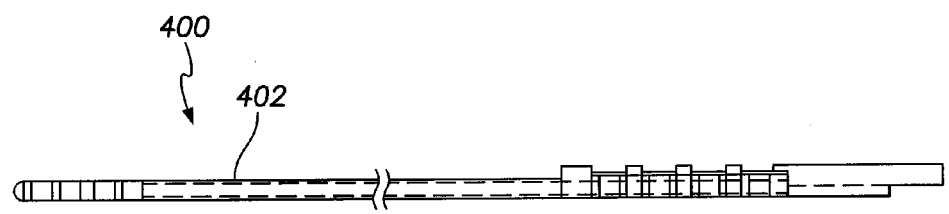
FIG. 14 illustrates a lateral view of a therapeutic probe, according to an embodiment of the present disclosure.

FIG. 14 illustrates a lateral view of a therapeutic probe 400, according to an embodiment of the present disclosure. The therapeutic probe 400 is configured to be operatively connected to DBS positioning sub-system 16 (shown in FIG. 1A). After the positioning probe 340 is removed from the patient, the therapeutic probe 400 may be inserted into the burr hole into the brain to the target area by way of the path confirmed by the positioning probe 340. As one example, the positioning probe 340 may be removed from a guide tube, and the therapeutic probe 400 may be inserted into the guide tube and connect to the target area to emit therapeutic energy into the target area. The therapeutic probe 400 may include a macroelectrode that may generally have a larger cross-sectional diameter than the electrode of the positioning probe 340.

Figure 15:
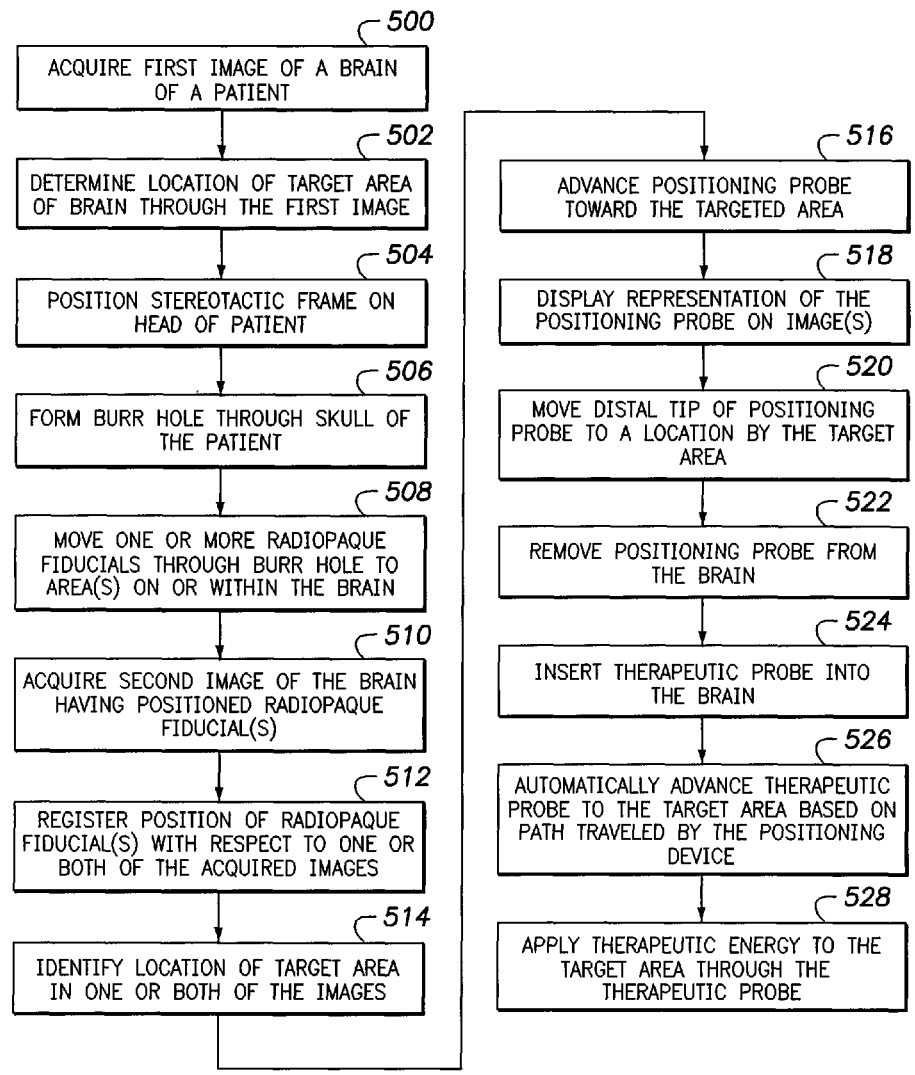
FIG. 15 illustrates a flow chart of a method of performing a deep brain stimulation (DBS) surgery, according to an embodiment of the present disclosure.

FIG. 15 illustrates a flow chart of a method of performing a DBS surgery, according to an embodiment of the present disclosure. At 500, a first image of a brain of a patient is acquired. For example, an MRI image of the patient's brain may be acquired.

At 502, the image may be referenced in order to determine a location of a target area of brain for therapy. Then, at 504, a stereotactic frame may be positioned on the head of the patient. At 506, a surgical drill may be used in conjunction with the stereotactic frame to form a burr hole through the skull of the patient. The position of the burr hole may be determined through analysis of the target area as shown in the image. The analysis may be performed by a surgeon or automatically through an imaging and/or surgical navigation sub-system. Notably, brain shift may occur after the burr hole is formed.

After the burr hole is formed, one or more radiopaque fiducials are moved through the burr hole to area(s) on or within the brain at 508. For example, the fiducials may be secured to one or more positioning probes that are positioned on or within the brain through a driving mechanism connected to the stereotactic frame. Because the burr hole has already been formed, the brain may have already shifted and settled.

At 510, a second image of the brain with the fiducials positioned thereon or therein is acquired. The image is acquired subsequent to any brain shift that may occurred during formation of the burr hole.

Then, at 512, the position(s) of the radiopaque fiducial(s) is registered with respect to one or both of the acquired images. For example, the fiducial(s) may be registered in relation to anatomical markers of the brain that are shown in the images. At 514, the location of the target area is identified in one or both of the images. For example, the images may be merged together and the target location identified in the merged image.

At 516, the positioning probe is advanced toward the targeted area. The positioning probe includes a position detector within the presence of a field, such as a magnetic field. The surgical navigation sub-system detects the presence of the position detector within the field and displays the position of the positioning probe on the displayed image(s). At 518, a representation of the positioning probe is shown on the image(s), which is shown on a display or monitor. By tracking the real time movement of the positioning probe on the display, a distal tip of the positioning probe may be moved to a location by the target area at 520. For example, the distal tip may be moved to a position that is 1-5 mm away from the target area. Alternatively, a recording contact may be used to record physiological phenomena, such as frequencies emitted by the target area, as an accuracy check for the visualization of the positioning probe to the target area.

After being positioned proximate to the target area, the positioning probe may then be removed at 522. For example, the positioning probe may be removed from a guide tube. Then, at 524, a therapeutic probe may be inserted into the brain, such as through the guide tube.

At 526, the therapeutic probe may be automatically advanced to the target area based on the path traveled by the positioning probe. In at least one embodiment, the guide tube that conveyed the positioning probe may remain in place and used to move the therapeutic probe into position. Optionally, the surgical navigation sub-system and/or the DBS positioning sub-system may store the path traveled by the positioning probe and automatically advance the therapeutic probe along the same path to the target area. Once the therapeutic probe is moved into contact with the target area, the therapeutic energy may be applied through the therapeutic probe to the target area at 528.

Alternatively, the positioning probe and the therapeutic probe may be one in the same. For example, instead of using separate and distinct probes, a single probe may be positioned within the brain, as described, and configured to provide therapy to the target area. As such, instead of removing a positioning probe, the positioning probe is moved into contact with the target area and used to apply therapeutic energy to the target area.

Figure 16:
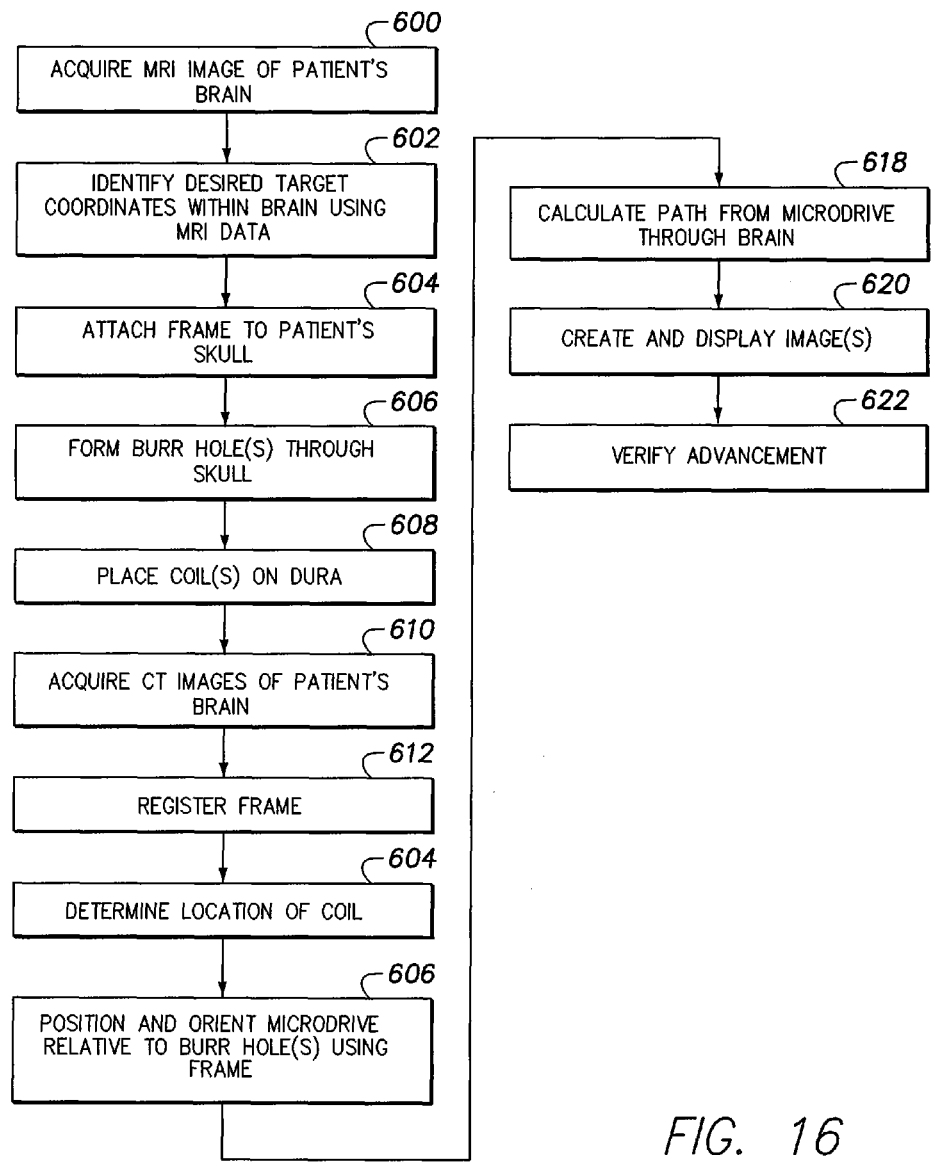
FIG. 16 illustrates a flow chart of a method of performing a deep brain stimulation (DBS) surgery, according to an embodiment of the present disclosure.

FIG. 16 illustrates a flow chart of a method of performing a DBS surgery, according to an embodiment of the present disclosure. The method shown and described with respect to FIG. 16 may not use radiopaque fiducials within a skull. Additionally, the method shown and described with respect to FIG. 16 may not use a fluoroscopic imaging system.

The method begins at 600, in which one or more MRI images of a patient's brain are acquired. Next, at 602, desired target coordinates within the brain are identified using MRI data from the MRI image(s).

At 604, a stereotactic frame is attached to the patient's skull. Then, at 606, one or more burr hole(s) are formed through the patient's skull, using the stereotactic frame and a surgical device, such as a surgical drill.

At 608, one or more coils may then be placed on a portion of the patient's brain, such as the dura, through the burr hole(s). After the coil(s) is placed on the dura, for example, one or more CT images of the patient's brain are acquired at 610. The CT image(s) establish the relative location of the coil(s) on the dura relative to brain structures.

The stereotactic frame is then registered at 612. The frame is registered to determine the absolute location of the frame in the procedure room. Then, at 614, the location of the coil(s) is determined. The absolute location of the coil(s) may be determined in the procedure room using an electromagnetic field and location system, such as described in U.S. Pat. No. 7,811,294. The coil location determination operation of 614 may be repeated during an implant procedure as deemed necessary.

At 616, a microdrive may be positioned and oriented relative to the burr hole(s) using the stereotactic frame. At 618, a path from the microdrive through the brain is calculated. For example, the path may be calculated using a determined location of the frame, microdrive position/orientation on the frame, the determined location of the coil(s), relative location of the coil(s) to brain structure(s) through CT data, location of target coordinates identified through MRI data, and/or the like.

At 620, image(s) are created and displayed. For example, image(s) of a probe or lead may be superimposed and tracked over the MRI image(s) as the probe or lead is advanced by the microdrive through the brain using the calculated path. At 622, the advancement of the probe or lead through the brain is verified. For example, microelectrode recordings through the path may be used to verify the advancement of the probe or lead.

The embodiment shown and described in FIG. 16 provides an objective determination of a position of a microelectrode or stimulation probe or lead without use of a fluoroscopic imaging system, for example. Further, the embodiment shown and described eliminates brain shift error that may otherwise be inherent when correlating a stereotactic frame and microdrive advancement with prior MRI images.

Various embodiments described herein provide a tangible and non-transitory (for example, not an electric signal) machine-readable medium or media having instructions recorded thereon for one or more processors or computers to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the sub-systems, systems, control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" may be interchangeable, and include any computer program stored in memory for execution by a computer, including RAM memory, ROM memory, EEPROM memory, and non-volatile RAM (NVRAM) memory. The above memory types are exemplary only, and are thus not limiting as to the types of memory usable for storage of a computer program.

Referring to FIGS. 1A-16, embodiments of the present disclosure provide systems and methods that may automate phases of DBS surgery, and/or allow visualization of lead or probe insertion. Embodiments of the present disclosure provide systems and methods that may automate surgical planning and lead or probe placement, while providing a surgeon a real-time three-dimensional rendered display of the current lead or probe position within the brain, thereby improving positioning of the lead or probe, reducing surgery time, and reducing the likelihood of adverse surgical events, such as brain hemorrhaging.

Certain embodiments of the present disclosure provide a system and method that may include one or more position detectors, such as coils, and one or more radiopaque fiducials positioned on a stereotactic frame and/or on or within the brain. The position detectors and/or the radiopaque fiducials may be registered with one or more images so that the image coordinates may be related to spatial coordinates of the surgical navigation sub-system. As such, registration of the coordinates of the stereotactic frame may be registered to the one or more images, thereby registering the one or more images to the spatial coordinates of the surgical navigation sub-system.

Certain embodiments of the present disclosure provide one or more probes including a position detector configured to be detected by a surgical navigation sub-system. Accordingly, movement of the probe through the brain may be shown as the probe is moved through the brain. The probe(s) may also include a recording contact that may be used as an accuracy check in relation to the tracked movement of the probe(s) by the surgical navigation sub-system.

Certain embodiments of the present disclosure provide systems and methods configured to automatically advance a probe to a target area within the brain.

Embodiments of the present disclosure provide a system and method in which a brain is imaged after a burr hole is formed through a skull and a fiducial is positioned thereon or therein. As such, embodiments of the present disclosure may detect and account for any brain shift before the positioning probe is advanced further into the brain.

Embodiments of the present disclosure provide systems and methods that reduce surgical time, improve surgical accuracy, and reduce collateral surgical adversity, such as brain hemorrhaging.

While various spatial and directional terms, such as top, bottom, lower, mid, lateral, horizontal, vertical, front, and the like may be used to describe embodiments, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for performing deep brain stimulation (DBS) therapy, the method comprising:
  acquiring at least one first image of a brain of a patient with at least one imaging sub-system;
  determining a location of a target area for therapy in the at least one first image;
  forming a burr hole through a skull of the patient based on the location the target area;
  positioning one or more reference members on or within the brain through the burr hole;
  acquiring at least one second image of the brain having the one or more reference members;

registering a position of the one or more reference members with one or both of the at least one first image and the at least one second image using a registration module;

tracking movement of at least one probe within the brain based on the registering operation with a tracking module; and displaying movement of a representation of the at least one probe on the one or both of the at least one first image and the at least one second image based on the tracking operation with a display module.

2. The method of claim 1, wherein the one or more reference members comprises one or more radiopaque fiducials.

3. The method of claim 1, wherein the one or more reference members comprises one or more position-detecting coils.

4. The method of claim 1, further comprising:

positioning a stereotactic frame on a head of the patient, wherein the forming a burr hole operation includes aligning a drill with the head of the patient with the stereotactic frame; and using a moving mechanism and the stereotactic frame to control movement of the at least one probe into and within the brain.

5. The method of claim 1, wherein the at least one probe comprises at least one positioning probe having the one or more reference members.

6. The method of claim 5, wherein the at least one positioning probe further comprises a recording contact configured to record electrophysiological phenomena.

7. The method of claim 1, wherein the at least one probe comprises at least one therapeutic probe configured to deliver therapeutic energy to the target area.

8. The method of claim 1, further comprising automatically moving the at least one probe into and within the brain toward the target area using a surgical navigation sub-system.

9. A system for performing deep brain stimulation (DBS) therapy, the system comprising:

at least one imaging sub-system configured to acquire at least one first image of a brain of a patient, wherein a location of a target area for therapy is determined from the at least one first image;

one or more reference members positioned on or within the brain through a pre-formed burr hole, wherein the at least one imaging sub-system is configured to acquire at least one second image of the brain having the one or more reference members;

a registration module configured to register a position of the one or more reference members with one or both of the at least one first image and the at least one second image;

at least one probe configured to be moved into and within the brain;

a tracking module configured to track movement of the at least one probe within the brain based on the registration of the position of the one or more reference members with the one or both of the at least one first image and the at least one second image; and a display module configured to display movement of a representation of the at least one probe on the one or both of the at least one first image and the at least one second image based on the tracked movement of the at least one probe.

10. The system of claim 9, wherein the one or more reference members comprises one or more radiopaque fiducials.

11. The system of claim 9, wherein the one or more reference members comprises one or more position-detecting coils.

12. The system of claim 9, further comprising:

a stereotactic frame positioned on a head of the patient, wherein the burr hole is formed with a drill positioned with respect to the stereotactic frame; and a moving mechanism that controls movement, in conjunction with the stereotactic frame, of the at least one probe into and within the brain.

13. The system of claim 9, wherein the at least one probe comprises at least one positioning probe having the one or more reference members.

14. The system of claim 13, wherein the at least one positioning probe further comprises a recording contact configured to record electrophysiological phenomena.

15. The system of claim 9, wherein the at least one probe comprises at least one therapeutic probe configured to deliver therapeutic energy to the target area.

16. The system of claim 9, wherein the at least one probe is automatically moved into and within the brain toward the target area.

17. The system of claim 9, wherein the at least one imaging sub-system comprises:

a magnetic resonance imaging (MRI) sub-system configured to acquire the at least one first image as at least one MRI image; and and a computed tomography (CT) sub-system configured to acquire the at least one second image as at least one CT image.

18. The system of claim 17, wherein the display module merges the at least one MRI image with the at least one CT image to form a merged image, and wherein the display module is configured to display movement of the representation of the at least one probe on the merged image.

* * * * *